United States Patent
Nakashima et al.

(10) Patent No.: US 10,292,941 B2
(45) Date of Patent: May 21, 2019

(54) ADHESIVE PATCH

(71) Applicant: HISAMITSU PHARMACEUTICAL CO., INC., Tosu-shi, Saga (JP)

(72) Inventors: Kentaro Nakashima, Tosu (JP); Masahiro Sato, Tosu (JP); Yasuhisa Kose, Tosu (JP); Takaaki Yoshinaga, Tosu (JP)

(73) Assignee: HITSAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 15/547,645

(22) PCT Filed: Feb. 5, 2016

(86) PCT No.: PCT/JP2016/053456
§ 371 (c)(1),
(2) Date: Jul. 31, 2017

(87) PCT Pub. No.: WO2016/125878
PCT Pub. Date: Aug. 11, 2016

(65) Prior Publication Data
US 2018/0015049 A1 Jan. 18, 2018

(30) Foreign Application Priority Data
Feb. 5, 2015 (JP) ................................ 2015-021411

(51) Int. Cl.
| | |
|---|---|
| *A61K 9/70* | (2006.01) |
| *B32B 5/02* | (2006.01) |
| *A61F 13/00* | (2006.01) |
| *A61F 13/02* | (2006.01) |
| *A61K 47/06* | (2006.01) |
| *A61K 47/34* | (2017.01) |
| *B32B 27/00* | (2006.01) |
| *A61K 31/045* | (2006.01) |
| *A61K 31/618* | (2006.01) |

(52) U.S. Cl.
CPC ...... *A61K 9/7053* (2013.01); *A61F 13/00063* (2013.01); *A61F 13/02* (2013.01); *A61F 13/0243* (2013.01); *A61F 13/0253* (2013.01); *A61K 31/045* (2013.01); *A61K 31/618* (2013.01); *A61K 47/34* (2013.01); *B32B 5/02* (2013.01); *B32B 27/00* (2013.01); *A61K 9/7076* (2013.01); *A61K 47/06* (2013.01)

(58) Field of Classification Search
None
See application file for complete search history.

(56) References Cited

U.S. PATENT DOCUMENTS

| | | | |
|---|---|---|---|
| 6,914,169 B1 | 7/2005 | Oota et al. | |
| 2002/0031542 A1 | 3/2002 | Takada et al. | |
| 2007/0277806 A1* | 12/2007 | Dodo | A61F 7/034 126/263.02 |
| 2012/0029446 A1* | 2/2012 | Amano | A61K 9/7084 604/304 |
| 2012/0234484 A1* | 9/2012 | Takada | A61F 13/0008 156/250 |

FOREIGN PATENT DOCUMENTS

| | | |
|---|---|---|
| JP | S61-145112 A | 7/1986 |
| JP | H7-215847 A | 8/1995 |
| JP | H9-124463 A | 5/1997 |
| JP | H9-143059 A | 6/1997 |
| JP | 2001-238935 A | 11/2001 |
| JP | 2001-328935 A | 11/2001 |
| JP | 2004-143052 A | 5/2004 |
| JP | 2007-7062 A | 1/2007 |
| JP | 2007-008927 A | 1/2007 |
| JP | 2010-241030 A | 10/2010 |
| JP | 2013184977 A | 9/2013 |
| KR | 20020089476 A | 11/2002 |
| KR | 20020091273 A | 12/2002 |
| KR | 20030030995 A | 4/2003 |
| KR | 20070110433 A | 11/2007 |
| WO | 2016/125878 A1 | 8/2016 |

OTHER PUBLICATIONS

International Preliminary Report on Patentability issued in corresponding International Application No. PCT/JP2016/053456.
International Search Report dated Mar. 8, 2016 issued in corresponding International Application No. PCT/JP2016/053456.
Office Action dated Jun. 7, 2018 issued in corresponding Korean Application No. 10-2017-7024402.
European Patent Search Report dated Aug. 21, 2018 in corresponding European Patent Application No. 16746709.1.

* cited by examiner

*Primary Examiner* — Robert A Wax
*Assistant Examiner* — Randeep Singh
(74) *Attorney, Agent, or Firm* — Nath, Goldberg & Meyer; Tanya E. Harkins; Joshua B. Goldberg

(57) ABSTRACT

Disclosed is an adhesive patch having a support and an adhesive agent layer laminated on the support, wherein the support consists of spunlace nonwoven fabric, the adhesive agent layer comprises an SIS block copolymer and liquid paraffin, the adhesive patch has a first direction, which is a predetermined reference axis direction, and a second direction, which is orthogonal to the first direction, and a bending resistance in the first direction of the adhesive patch is 18 to 30 mm.

6 Claims, No Drawings

ADHESIVE PATCH

This is a National Phase Application filed under 35 U.S.C. 371 as a national stage of PCT/JP2016/053456, filed Feb. 5, 2016, an application claiming the benefit of Japanese Application No. 2015-021411, filed Feb. 5, 2015, the content of each of which is hereby incorporated by reference in its entirety.

TECHNICAL FIELD

The present invention relates to an adhesive patch.

BACKGROUND ART

To alleviate shoulder, elbow, and knee pain, an emplastrum adhesive patch (plaster) is commercially available in which an adhesive agent layer containing a drug such as an anti-inflammatory analgesic is laminated on a support. Among such adhesive patches, adhesive patches that use woven fabric for the support have excellent stretchability and tend to conform to the stretching of the skin, and thus have excellent adherability. However, adhesive patches that use woven fabric for the support tend to have poor so-called "firmness". Therefore, when applying the adhesive patch to the affected area, the adhesive surfaces of the adhesive patch may stick to each other if the adhesive patch abruptly loops back on itself, and hence the adhesive patches tend to be difficult to apply.

On the other hand, adhesive patches that use nonwoven fabric for a support have also been developed. Compared with adhesive patches that use woven fabric for a support, adhesive patches that use nonwoven fabric for a support tend to improve on the problem of "firmness", but the components of the adhesive agent layer tend to exude out from the support due to the occurrence of so-called cold flow.

CITATION LIST

Patent Literature

[Patent Literature 1] Japanese Unexamined Patent Publication

SUMMARY OF INVENTION

Technical Problem

It is an object of the present invention to provide an adhesive patch that is easy to apply and that does not exude components of an adhesive agent layer from a support.

Solution to Problem

In view of the above-mentioned circumstances, the present inventors carried out diligent investigations, and as a result discovered that the above-mentioned problems could be solved by combining a support consisting of spunlace nonwoven fabric and an adhesive agent layer comprising a styrene-isoprene-styrene block copolymer and liquid paraffin, and setting a bending resistance of the adhesive patch to 18 to 30 mm.

In other words, the present invention provides an adhesive patch comprising a support; and an adhesive agent layer laminated on the support, wherein the support consists of spunlace nonwoven fabric, the adhesive agent layer comprises a styrene-isoprene-styrene block copolymer and liquid paraffin, the adhesive patch has a first direction, which is a predetermined reference axis direction, and a second direction, which is orthogonal to the first direction, and a bending resistance in the first direction of the adhesive patch measured by a 45° cantilever method defined in JIS L 1085:1998 is 18 to 30 mm.

A mass ratio of the styrene-isoprene-styrene block copolymer to the liquid paraffin in the adhesive agent layer may be 1 to 1.65:1. The adhesive agent layer may comprise methyl salicylate and menthol. The adhesive agent layer may comprise polyisobutylene. The adhesive agent layer may comprise a terpene resin. The adhesive agent layer may comprise, based on a total mass of the adhesive agent layer, 9 to 11% by mass of methyl salicylate and 2.5 to 6.5% by mass of menthol. Further, the adhesive agent layer may comprise, based on a total mass of the adhesive agent layer, 23.7 to 32.5% by mass of the styrene-isoprene-styrene block copolymer, 17.9 to 27.5% by mass of liquid paraffin, 9 to 11% by mass of methyl salicylate, 3 to 6% by mass of menthol, 3 to 12% by mass of polyisobutylene, and 17 to 25% by mass of the terpene resin.

In addition, a basis weight of the nonwoven fabric may be 90 to 110 $g/m^2$. A 20% modulus in a width direction of the nonwoven fabric may be 3 to 5 N/50 mm. A 50% modulus in a width direction of the nonwoven fabric may be 8 to 15 N/50 mm. The nonwoven fabric may comprise a polyester. The bending resistance in the first direction of the adhesive patch measured by a 45° cantilever method defined in JIS L 1085:1998 may be 18 to 27 mm.

Advantageous Effects of Invention

The adhesive patch according to the present invention is easy to apply due to its "firmness". Further, the components of the adhesive agent layer are less susceptible to cold flow.

DESCRIPTION OF EMBODIMENTS

The adhesive patch according to the present embodiment has a support and an adhesive agent layer laminated on the support. The support consists of spunlace nonwoven fabric, and the adhesive agent layer comprises a styrene-isoprene-styrene block copolymer and liquid paraffin. The adhesive patch has a first direction, which is a predetermined reference axis direction, and a second direction, which is orthogonal to the first direction. A bending resistance in the first direction of the adhesive patch is 18 to 30 mm.

In the present specification, the term "bending resistance" means the bending resistance measured by a 45° cantilever method defined in JIS L 1085:1998. In other words, the bending resistance means the distance (mm) that a 2 cm-wide test piece (adhesive patch or support) arranged on a horizontal table with a smooth surface having a 45° incline and a scale on an upper face thereof such that the shorter side of the test piece and the baseline of the scale coincide with each other slides until a center point of one of the shorter sides of the test piece comes into contact with the inclined face when the test piece is gently slid in the direction of the inclined face. The bending resistance in the first direction of the adhesive patch means the bending resistance when the test piece is gently slid across the inclined face in the first direction.

The term "spunlace nonwoven fabric" means a nonwoven fabric formed by a so-called hydroentanglement method, in which the fibers are entangled by spraying high-pressure jets of water at the fibers. The raw material for the spunlace nonwoven fabric is a synthetic resin, for example, polyesters such as polyethylene terephthalate (PET), polyolefins such as an ethylene/vinyl acetate copolymer (EVA), vinyl chloride, polyethylene, and polypropylene, a butadiene/styrene/methyl methacrylate copolymer resin, nylon, polyurethane, an alkoxyalkyl (meth)acrylate copolymer, polyvinyl acetal, polyamide, and rayon, and natural materials such as cotton, wool, and silk. From the perspective of ease of application of the adhesive patch, it is preferred that the spunlace nonwoven fabric be a spunlace nonwoven fabric comprising polyester. It is preferred that a diameter of the fibers be 5 to 1.5 μm.

A basis weight of the spunlace nonwoven fabric is, for example, 50 g/m² or more, preferably 70 g/m² or more, and more preferably 90 g/m² or more. When the basis weight value of the spunlace nonwoven fabric is equal to or more than this lower limit, it is more difficult for the components of the adhesive agent layer to exude out. The basis weight of the spunlace nonwoven fabric is, for example, 200 g/m² or less, preferably 150 g/m² or less, and more preferably 125 g/m² or less. When the basis weight value is equal to or less than this upper limit, a sense of discomfort is less likely to be produced when the adhesive patch is adhered. From the perspective of ease of application of the adhesive patch, it is especially preferred that the basis weight of the spunlace nonwoven fabric be 90 to 110 g/m² or 100 to 110 g/m².

The spunlace nonwoven fabric has a machine direction (flow direction or longitudinal direction) and a cross direction (width direction or transverse direction). A stretchability of the spunlace nonwoven fabric has, for example, a 50% modulus in the flow direction of 200 to 400 N/50 mm, and a 50% modulus in the width direction of 5 to 15 N/50 mm. Measurement of the stretchability is based on the load for stretching under fixed elongation as defined in JIS L 1096: 2010. When the stretchability of the spunlace nonwoven fabric is within the above-mentioned range, it is easier for the applying portion of the adhesive patch to conform to the stretching of the skin. From the perspective of ease of application of the adhesive patch, it is preferred that the stretchability of the spunlace nonwoven fabric have a 20% modulus in the flow direction of 40 to 90 N/50 mm, and more preferably 55 to 75 N/50 mm, a 20% modulus in the width direction of 3 to 5 N/50 mm, and more preferably 3.6 to 4.4 N/50 mm, a 50% modulus in the flow direction of 150 to 350 N/50 mm, and more preferably 220 to 300 N/50 mm, and a 50% modulus in the width direction of 8 to 15 N/50 mm, and more preferably 11.2 to 11.7 N/50 mm. It is preferred that the width direction and the flow direction of the spunlace nonwoven fabric respectively match the first direction and the second direction of the adhesive patch.

It is preferred that the bending resistance of the spunlace nonwoven fabric be 18 to 30 mm. When the bending resistance in the width direction of the spunlace nonwoven fabric is within this range, when an adhesive patch in Which an adhesive agent layer is laminated on a support consisting of spunlace nonwoven fabric is produced, the bending resistance in the first direction of the adhesive patch can be easily set with the desired range. It is preferred that the bending resistance in the first direction of the spunlace nonwoven fabric be 18 to 30 mm, and from the perspective of ease of application of the adhesive patch, be 18 to 27 mm or 21 to 27 mm.

As the support, products that are commercially available as spunlace, nonwoven fabrics can be used. Examples of products include products sold by Unitika Ltd., Kuraray Kuraflex Co., Ltd., Yuho Co., Ltd., Daiwabo Polytec Co., Ltd., and Japan Vilene Company, Ltd.

The adhesive agent layer comprises a styrene-isoprene-styrene block copolymer (hereinafter sometimes referred to as SIS or an SIS block copolymer and liquid paraffin. Combining an adhesive agent layer comprising these components with a spunlace nonwoven fabric enables the "firmness" of the adhesive patch to be strengthened, which allows the adhesive patch to apply more easily.

A commercially-available product can be used for the SIS block copolymer. Examples thereof include Cariflex TR-1107, Cariflex TR-1111, TR-1112, and Cariflex TR-1117 (all of which are manufactured by Shell Chemicals K.K., as well as JSR 5000, JSR 5002, JSR 5100 (all of which are manufactured by JSR Corporation) and Quintac 3570 C (manufactured by Zeon Corporation).

The content of the SIS block copolymer in the adhesive agent layer is, based on the total mass of the adhesive agent layer, for example, 10% by mass or more, preferably 15% by mass or more, and more preferably 20% by mass or more. An adhesive patch comprising an adhesive agent layer comprising an SIS block copolymer in an amount that is equal to or more than the above-mentioned lower limit does not peel away from the skin during the required adhesion duration, and has sufficient "firmness". The content of the SIS block copolymer in the adhesive agent layer is, based on the total mass of the adhesive agent layer, for example, 50% by mass or less, preferably 40% by mass or less, and more preferably 30% by mass or less. An adhesive patch comprising an adhesive agent layer that comprises an SIS block copolymer in an amount equal to or less than the above-mentioned upper limit has excellent usability, such as not causing pain when the adhesive patch is peeled off. From the perspective of ease of application of the adhesive patch, it is particularly preferred for the content of the SIS block copolymer in the adhesive agent layer to be 23.7 to 32.5% by mass.

The content of the liquid paraffin in the adhesive agent layer is, based on the total mass of the adhesive agent layer, for example, 5% by mass or more, preferably 10% by mass or more, and more preferably 15% by mass or more. An adhesive patch comprising an adhesive agent layer that comprises liquid paraffin in an amount equal to or more than the above-mentioned lower limit has sufficient pressure-sensitive adhesion. The content of the liquid paraffin in the adhesive agent layer is, based on the total mass of the adhesive agent layer, for example, 50% by mass or less, preferably 40% by mass or less, and more preferably 30% by mass or less. An adhesive patch comprising an adhesive agent layer that comprises liquid paraffin in an amount equal to or less than the above-mentioned lower limit has appropriate flexibility, and hence is easy to apply. From the perspective of ease of application of the adhesive patch, it is especially preferred for the content of the liquid paraffin in the adhesive agent layer to be 17.9 to 27.5% by mass.

Further, it is preferred that the mass ratio between the SIS block copolymer and the liquid paraffin in the adhesive agent layer be 1 to 1.65:1. When those components are blended in such a ratio, "firmness" of the adhesive patch can be strengthened, and the adhesive patch is easier to apply. In addition, when those components are blended in such a ratio, the adhesive agent layer can be adjusted to an appropriate stiffness, air-bubble voids are less likely to form in the adhesive agent layer during production, and production suitability is excellent. Still further, when those components are blended in such a ratio, it is also easier to prevent cold flow.

The adhesive agent layer may optionally comprise an adhesive agent other than SIS block copolymer and a plasticizer other than liquid paraffin. The adhesive agent layer may also comprise additives such as tackifiers, absorption accelerators, antioxidants, fillers, crosslinking agents, preservatives, ultraviolet absorbers, surfactants, pH adjusters, pigments, and perfumes.

Examples of adhesive agents other than the SIS block copolymer comprise natural rubber, synthetic isoprene rubber, polyisobutylene, polyvinyl ether, polyurethane, polyisoprene, polybutadiene, a styrene-butadiene copolymer, and a styrene-isoprene copolymer. It is preferred for the adhesive agent layer to comprise polyisobutylene. Using polyisobutylene enables the adhesive agent three to be improved. The content of the polyisobutylene in the adhesive agent layer is, for example, 1 to 20% by mass, and preferably 2 to 15% by mass. From the perspective of ease of application of the adhesive patch, it is especially preferred that the content of the polyisobutylene in the adhesive agent layer be 3 to 12% by mass.

Examples of plasticizers other than liquid paraffin include polybutene, liquid polyisobutylene, and animal and vegetable oils.

Examples of plasticizers include alicyclic saturated hydrocarbon resins (manufactured by Arakawa Chemical industries, Ltd. under the trade names of Arkon P-100 etc.), hydrogenated rosin esters (manufactured by Arakawa Chemical Industries, Ltd. under the trade names KE-311 and KE-100, and manufactured by Hercules Incorporated under the trade names Foral 105, Foral 85, etc.), hydrogenated alicyclic hydrocarbons (manufactured by Exxon Chemical Co. under the trade names of Escorez 5300 etc.), terpene resins, petroleum resins, and phenol resins. Among those tackifiers, a terpene resin consisting of αpinene, β-pinene, and the like is preferred, because such a terpene resin has an excellent effect of increasing adhesive force. When the SIS block copolymer and the liquid paraffin are blended in the adhesive agent layer in a ratio of 1 to 1.65:1, the adhesive force of the adhesive agent layer tends to decrease. In such a case, the adhesive three can be improved through the effect of the terpene resin. From the perspective of improving the adhesive force, it is especially preferred for the content of the terpene resin in the adhesive agent layer to be 17 to 25% by mass.

Examples of absorption accelerators include isopropyl myristate, diethyl sebacate, sorbitan monolaurate, sodium oleyl phosphate, sodium lauryl sulfate, octyl phenyl ether, lauryl ether, sorbitan monolaurate, lauryl diethanol amide, lauroyl sarcosine, oleoyl sarcosine sugar ester, lecithin, glycyrrhetinic acid, urea, salicylic acid, calcium thioglycolate, lactic acid, lactic acid ester, olive oil, squalene, lanolin, and glycerin.

Examples of antioxidants include tocopherol and ester derivatives thereof, ascorbic acid, ascorhyl stearate, nordihydroguaiaretic acid, dibutylhydroxytoluene, and butylhydroxyanisole.

Examples of fillers include calcium carbonate, magnesium carbonate, silicate (e.g., aluminum silicate, magnesium silicate etc.), silicic acid, barium sulfate, calcium sulfate, calcium zincate, zinc oxide, titanium dioxide, and zinc stearate.

Examples of crosslinking agents include organic crosslinking agents such as a thermosetting resin (an amino resin, a phenol resin, an epoxy resin, an alkyd resin, unsaturated polyester etc.), an isocyanate compound, and a block isocyanate compound, and inorganic crosslinking agents such as a metal or a metal compound and the like.

Examples of preservatives include ethyl p-hydroxybenzoate, propyl p-hydroxybenzoate, and butyl p-hydroxybenzoate.

Examples of ultraviolet absorbers include para-aminobenzoic acid derivatives, anthranilic acid derivatives, salicylic acid derivatives, coumarin derivatives, amine-acid compounds, imidazoline derivatives, pyridine derivatives, and dioxane derivatives.

Examples of the drug to be contained in the adhesive agent layer may include, but are not limited to: an anti-inflammatory analgesic drug such as acetaminophen, phenacetin, mefenamic acid, diclofenac sodium, flufenamic acid, aspirin, sodium salicylate, methyl salicylate, glycol salicylate, aminopyrine, alclofenac, ibuprofen, naproxen, flurbiprofen, ketoprofen, amfenac sodium, mepirizole, indomethacin, piroxicam, and felbinac; a steroidal anti-inflammatory drug such as hydrocortisone, triamcinolone, dexamethasone, and prednisolone; a vasodilator drug such as diltiazem hydrochloride, pentaerythritol tetranitrate, isosorbide dinitrate, trapidil, nicorandil, nitroglycerin, prenylamine lactate, molsidomine, aluminum nitrite, tolazoline hydrochloride, and nifedipine; a drug for arrhythmia such as procainamide hydrochloride, lidocaine hydrochloride, propranolol hydrochloride, alprenolol hydrochloride, atenolol, nadolol, metoprolol tartrate, ajmaline, disopyramide, and mexiletine hydrochloride; an antihypertensive agent such as ecarazine hydrochloride, indapamide, clonidine hydrochloride, bunitrolol hydrochloride, labetalol hydrochloride, captopril, guanabenz acetate, mebutamate, and betanidine sulfate; a cough medication and expectorant such as carbetapentane citrate, cloperastine, oxeladin tannate, clobutinol hydrochloride, clofedanol hydrochloride, noscapine hydrochloride, ephedrine hydrochloride, isoproterenol hydrochloride, clorprenaline hydrochloride, methoxyphenamine hydrochloride, procaterol hydrochloride, tulobuterol hydrochloride, clenbuterol hydrochloride, and ketotifen fumarate; an antineoplastic drug such as cyclophosphamide, fluorouracil, tegafur, mitomycin C, procarbazine hydrochloride, doxifluridine, and ranimustine; a topical anesthetic such as ethyl aminobenzoate, tetracaine hydrochloride, procaine hydrochloride, dibucaine hydrochloride, oxybuprocaine hydrochloride, and propitocaine hydrochloride; a hormone drug such as propylthiouracil, thiamazole, methenolone acetate, estradiol, estriol, and progesterone; an antihistamine drug such as diphenhydramine hydrochloride, chlorpheniramine maleate, promethazine, cyproheptadine hydrochloride, and diphenylpyraline hydrochloride; an anticoagulant drug such as warfarin potassium and ticlopidine hydrochloride; an antispasmodic drug such as atropine methylbromide and scopolamine; a general anesthetic such as thiopental sodium and pentobarbital sodium; a hypnotic-analgesic drug such as bromovalerylurea, amobarbital, and phenobarbital; an antiepileptic drug such as phenytoin sodium; a stimulant/analeptic drug such as methamphetamine hydrochloride; an antidinic such as difenidol hydrochloride and betahistine mesylate; a drug for psychoneurosis such as chlorpromazine hydrochloride, thioridazine, meprobamate, imipramine hydrochloride, chlordiazepoxide, and diazepam; a skeletal muscle relaxant such as suxamethonium hydrochloride and eperisone hydrochloride; an autonomic drug such as neostigmine bromide and bethanechol chloride; an anti-parkinsonism drug such as amantadine hydrochloride; a diuretic drug such as hydroflumethiazide, isosorbide, and furosemide; a vasoconstrictor such as phenylephrine hydrochloride; a respiratory stimulant such as lobeline bromide, dimorpholamine, and naloxone hydrochloride; a peptic antiulcer drug such as glycopyrronium bromide, proglumide, cetraxate hydrochloride, cimetidine, and spizofurone; a cholagogue such as ursodesoxycholic acid and osalmid; a drug for the urogenital organ and anus such as hexamine, sparteine, dinoprost, and ritodrine hydrochloride; a drug for parasitic skin diseases such as salicylic acid, ciclopiroxolamine, and croconazole hydrochloride; a skin softener such as urea; a vitamin production such as calcitriol, thiamine hydrochloride, riboflavin sodium phosphate, pyridoxine hydrochloride, nicotinic acid amide, panthenol, and ascorbic acid; an inorganic formulation such as calcium chloride, potassium iodide, and sodium iodide; a hemostat such as ethamsylate; a drug for liver disease such as tiopronin; a drug for habitual toxicosis such as cyanamide; an arthrifuge such as colchicine, probenecid, and sulfinpyrazone; an antidiabetic such as tolbutamide, chlorpropamide, glymidine sodium, glybuzole, buformin hydrochloride, and insulin; an antibiotic such as benzylpenicillin potassium, propicillin potassium, cloxacillin sodium, sodium ampicillin, bacampicillin hydrochloride, carbenicillin sodium, cephaloridine, sodium cefoxitin, erythromycin, chloramphenicol, tetracycline, kanamycin sulfate, and cycloserine; a chemotherapeutic drug such as isocyanide, pyrazinamide, and ethionamide; and a narcotic such as morphine hydrochloride, codeine phosphate, cocaine hydrochloride, pethidine hydrochloride, and fentanyl citrate.

When high-concentration methyl salicylate and menthol (e.g., 1-menthol) are contained in the adhesive agent layer, due to the influence of those drugs, the tendency of the adhesive agent layer to become more plastic strengthens, which causes the "firmness" of the adhesive patch to weaken, and makes it more difficult fix the adhesive patch to apply. However, as described above, because the adhesive patch according to this embodiment has strong "firmness", the adhesive patch is easy to apply even when these drugs are comprised in the adhesive agent layer in high concentrations. In particular, application of the adhesive patch according to this embodiment is suitable when, based on the total mass of the adhesive agent layer, the adhesive agent layer comprises 9 to 11% by mass of methyl salicylate and 2.5 to 6.5% by mass or 3 to 6% by mass of menthol.

It is preferred that the thickness of the adhesive agent layer is 50 to 3000 μm. When the thickness of the adhesive agent layer is 3000 μm or less, release of the drug comprised in the adhesive agent layer is good, and when this thickness is 50 μm or more, skin adhesion is good, and the adhesive patch is less likely to peel off.

The thickness of the support is, for example, 300 μm or more, and preferably 400 μm or more. When the thickness of the support is a value equal to or more than this lower limit, it is more difficult for the components of the adhesive agent layer to exude out. Further, the thickness of the support is, for example, 1200 μm or less, and preferably 700 μm or less. When the thickness of the support is a value equal to or less than this upper limit, the adhesive patch is less likely to peel off.

It is preferred that the total of the thickness of the support and the thickness of the adhesive agent layer, namely, the thickness of the adhesive patch, is 300 to 5000 μm. When the thickness of the adhesive patch is 5000 μm or less, the edges of the adhesive patch are less likely to catch on clothes and the like, and the adhesive patch is less likely to peel off. When the thickness of the adhesive patch is 300 μm or more, the support properties of the adhesive patch are sufficient, the adhesive patch can be reliably adhered, and wrinkles do not occur as easily in the adhesive patch after being applied.

The adhesive patch according to this embodiment may be a rectangle or a rounded-corner rectangle having short sides of 4 to 10 cm and long sides of 6 to 15 cm. When the shape of the adhesive patch according to this embodiment is a rectangle or a rounded-corner rectangle, it is preferred that the long-side direction and the short side direction respectively match the width direction and the flow direction of the spunlace nonwoven fabric, and, match the first direction and the second direction of the adhesive patch.

The adhesive patch according to this embodiment may further comprise a release film for covering and protecting the adhesive agent layer. Examples of the material of the release film include plastic films such as cast polypropylene (CPP), oriented polypropylene (OPP), polyethylene terephthalate (PET), polybutylene terephthalate (PBT), polyethylene, polyester, polyurethane, polyvinyl chloride, and polystyrene, silicone-treated paper such as silicone-treated synthetic resin, synthetic paper, and synthetic fiber, aluminum foil, and laminate-processed paper in which polyethylene or the like is laminated on kraft paper. Of these, it is preferred for PET and treated paper to be used. When the adhesive patch comprises a release film, the bending resistance of the adhesive patch means the bending resistance measured for the adhesive patch in a state in which the release film has been peeled off.

The thickness of the release film is, for example, 10 to 100 μm preferably 30 to 90 μm, and more preferably 40 to 85 μm. When the thickness of the release film is a value equal to or more than the above-mentioned lower limit, the release film is easier to grab hold of, and the release film is less likely to cling to the adhesive agent layer when peeling oft the release film. On the other hand, when the thickness of the release film is a value equal to or less than the above-mentioned upper limit, cutting is easier during production, and the production suitability is good.

The adhesive patch according to this embodiment can be produced by a method known to a person skilled in the art. For example, using a mixing machine such as a kneader or a mixer, each of the components of the adhesive agent layer other than the drug is mixed while heating to 120 to 160° C., and then the drug is admixed into the mixture at a temperature at which the drug is not degraded to produce a mixture for forming the adhesive agent layer. This mixture may be directly spread onto the support to form the adhesive agent layer, or may be spread onto the release film to form the adhesive agent layer, the support placed thereon, and the adhesive agent layer transferred onto the support by pressure bonding.

EXAMPLES

Adhesive Patch Evaluation Test (1)

Each of the components in Table 1 were heated and kneaded to obtain an adhesive agent 1. The adhesive agent I was coated in a coating amount of 210 g/m² on the polyester nonwoven fabrics 2 to 4 shown in Table 2 to obtain the adhesive patches of Examples 1 and 2 and Comparative Example 1. The adhesive patches had a rectangular shape with a short-side length of about 5 cm and a long-side length of about 7 cm. Further, the width direction of the nonwoven fabrics and the long-side direction of the adhesive patches matched. The following evaluations were performed on the obtained adhesive patches. The results are shown in Table 4.

TABLE 1

| Adhesive Agent 1 | % by mass |
| --- | --- |
| SIS | 32.5 |
| Liquid Paraffin | 27.5 |
| Polyisobutylene | 3.0 |
| Terpene Resin | 17.0 |
| Methyl Salicylate | 10.0 |
| l-Menthol | 6.0 |
| Other Components | 4.0 |
| Total | 100 |

TABLE 2

| | Basis | | Bending Resistance in Width Direction (mm) | 20% Modulus (N/50 mm) | | 50% Modulus (N/50 mm) | |
| --- | --- | --- | --- | --- | --- | --- | --- |
| | Production method | Weight (g/m$^2$) | Thickness (μm) | | Flow Direction | Width Direction | Flow Direction | Width Direction |
| Nonwoven Fabric 1 | Needle Punch | 105 | 840 | 18 | — | — | 5.2 | 1.0 |
| Nonwoven Fabric 2 | Spunlace | 110 | 620 | 27 | 64.2 | 4.4 | 290.6 | 11.7 |
| Nonwoven Fabric 3 | Spunlace | 100 | 500 | 25 | 57.9 | 3.6 | 229.5 | 11.2 |
| Nonwoven Fabric 4 | Spunlace | 80 | 500 | 22 | 70.9 | 2.6 | 263.8 | 7.7 |

TABLE 3

| | Example 1 | Example 2 | Comparative Example 1 |
| --- | --- | --- | --- |
| Support | Nonwoven Fabric 2 | Nonwoven Fabric 3 | Nonwoven Fabric 4 |
| Adhesive Agent | Adhesive Agent 1 | Adhesive Agent 1 | Adhesive Agent 1 |

Adhesive Patch Evaluation Items
(1) Adhesive Patch Bending Resistance

The bending resistance in the long-side direction of the adhesive patch was measured based on a 45° cantilever method defined in JIS L 1085:1998.

(2) Ease of Application of Adhesive Patch

An adhesive patch was applied to a shoulder portion of 30 healthy adults. The ease of application was scored based on the following three-stage standard, and the average value of each adhesive patch was determined. Cases in which the average value was less than 2 were evaluated with an "A", and cases in Which the average value was 2 or more were evaluated with a "C".
1 Easy to apply
2 Normal
3 Difficult to apply (3) Adhesive Patch Adherability An adhesive patch was applied to a shoulder portion of 30 healthy adults. The adhesion state of the adhesive patch after 8 hours was scored based on the following three-stage standard, and the average value of each adhesive patch was determined. Cases in which the average value was less than 2 were evaluated with an "A", and cases in. which the average value was 2 or more were evaluated with a "C".
1 Adhesive patch had not peeled off at all, and was closely stuck to the skin
2 Only edge of the adhesive patch face had peeled off
3 One-quarter or more of the adhesive patch face had peeled off (4) Permeation (Exuding Out) of Adhesive Agent into Support The presence of permeation (exuding out) of the adhesive agent into the support was visually observed. Cases in which permeation (exuding out) was not found were evaluated with an "A", cases in which slight permeation (exuding out) was found but that would not be a problem if used as an adhesive patch were evaluated with a "B", and cases in which permeation (exuding out) was found and that would be unsuitable for use as an adhesive patch were evaluated with a "C".

(5) Production Suitability

The presence of air-bubble voids on the surface of the adhesive agent layer was visually observed. Cases in which there were no air-bubble voids were evaluated with an "A", and cases in which there were air-bubble voids were evaluated with a "C".

TABLE 4

| | Example 1 | Example 2 | Comparative Example 1 |
| --- | --- | --- | --- |
| Adhesive Patch Bending Resistance (mm) | 27 | 21 | 16 |
| Ease of Adhesion of Adhesive Patch | A | A | C |
| Adhesive Patch Adherability | A | A | A |
| Permeation of Adhesive Agent | A | A | A |
| Production Suitability | A | A | A |

From the results shown in Table 4, it is clear that the adhesive patches of Examples 1 and 2, in which the bending resistances of the adhesive patches were 18 or more, were excellent adhesive patches that were easy to apply and had excellent adherability, but did not exhibit permeation of the adhesive agent into the support. On the other hand, the adhesive patch of Comparative Example 1, in which the bending resistance of the adhesive patch was less than 18, was poor in terms of ease of application.

Adhesive Patch Evaluation Test (2)

Each of the components in Table 5 were heated and kneaded to obtain adhesive agents 2 to 6. The adhesive agents 2 to 6 were coated in a coating amount of 210 g/m$^2$ on the nonwoven fabrics 1 (made of polyester) and 3 shown in Table 2 to obtain the adhesive patches of Examples 3 to 7 and Comparative Examples 2 to 6. The same evaluations as performed in Evaluation Test (1) were carried out on the obtained adhesive patches. The results are shown in Table 7.

TABLE 5

|  | Adhesive Agent 2 | Adhesive Agent 3 | Adhesive Agent 4 | Adhesive Agent 5 | Adhesive Agent 6 |
| --- | --- | --- | --- | --- | --- |
| SIS | 37.0 | 29.5 | 25.0 | 23.7 | 23.4 |
| Liquid Paraffin | 18.9 | 17.9 | 23.7 | 23.7 | 27.2 |
| Polyisobutylene | 10.0 | 6.9 | 12.0 | 7.8 | 7.8 |
| Terpene Resin | 5.0 | 25.0 | 20.0 | 21.5 | 18.5 |
| Methyl Salicylate | 10.0 | 10.0 | 10.0 | 10.0 | 10.0 |
| l-Menthol | 6.0 | 6.0 | 3.0 | 6.0 | 6.0 |
| Other Components | 13.1 | 4.7 | 6.3 | 7.3 | 7.1 |
| Component Total | 100 | 100 | 100 | 100 | 100 |
| SIS:Liquid Paraffin | 1.96:1 | 1.65:1 | 1.05:1 | 1:1 | 0.86:1 |

(% by mass)

TABLE 6

|  | Example 3 | Example 4 | Example 5 | Example 6 | Example 7 |
| --- | --- | --- | --- | --- | --- |
| Support | Nonwoven Fabric 3 | Nonwoven Fabric 3 | Nonwoven Fabric 3 | Nonwoven Fabric 3 | Nonwoven Fabric 3 |
| Adhesive Agent | Adhesive Agent 2 | Adhesive Agent 3 | Adhesive Agent 4 | Adhesive Agent 5 | Adhesive Agent 6 |
|  | Comparative Example 2 | Comparative Example 3 | Comparative Example 4 | Comparative Example 5 | Comparative Example 6 |
| Support | Nonwoven Fabric 1 | Nonwoven Fabric 1 | Nonwoven Fabric 1 | Nonwoven Fabric 1 | Nonwoven Fabric 1 |
| Adhesive Agent | Adhesive Agent 2 | Adhesive Agent 3 | Adhesive Agent 4 | Adhesive Agent 5 | Adhesive Agent 6 |

TABLE 7

|  | Example 3 | Example 4 | Example 5 | Example 6 | Example 7 |
| --- | --- | --- | --- | --- | --- |
| Adhesive Patch Bending Resistance (mm) | 23 | 23 | 23 | 23 | 23 |
| Ease of Adhesion of Adhesive Patch | A | A | A | A | A |
| Adhesive Patch Adherability | A | A | A | A | A |
| Permeation of Adhesive Agent | A | A | A | A | B |
| Production Suitability | C | A | A | A | A |
|  | Comparative Example 2 | Comparative Example 3 | Comparative Example 4 | Comparative Example 5 | Comparative Example 6 |
| Adhesive Patch Bending Resistance (mm) | 20 | 20 | 20 | 20 | 20 |
| Ease of Adhesion of Adhesive Patch | C | C | C | C | C |
| Adhesive Patch Adherability | A | A | A | A | A |
| Permeation of Adhesive Agent | A | A | A | A | C |
| Production Suitability | C | A | A | A | A |

From the results shown in Table 7, it is clear that the adhesive patches of Comparative Examples 2 to 6, in which the nonwoven fabric 1 produced by a needle punch method was used as the support, were poor in terms of ease of application. On the other hand, the adhesive patches of Examples 3 to 7, in which the nonwoven fabric 3 produced by a spunlace method was used as the support, had excellent ease of application and adherability. Further, the adhesive patches of Examples 4 to 6, in which the mass ratio between the SIS and the liquid paraffin was in the range of 1 to 1.65:1, were also excellent in terms of production suitability and resistance to permeation of the adhesive agent into the support.

The invention claimed is:

1. An adhesive patch consisting essentially of:
   a support; and
   an adhesive agent layer laminated on the support, wherein
   the support consists of spunlace nonwoven fabric,
   the adhesive agent layer comprises, based on a total mass of the adhesive agent layer, a styrene-isoprene-styrene block copolymer in an amount of 23.7 to 32.5% by mass, liquid paraffin in an amount of 17.9 to 27.5% by mass, 9 to 11% by mass of methyl salicylate, 3 to 6% by mass of menthol, 3 to 12% by mass of polyisobutylene, and 17 to 25% by mass of a terpene resin, and a mass ratio of the styrene-isoprene-styrene block copolymer to the liquid paraffin in the adhesive layer is 1 to 1.65:1,
   the adhesive patch has a first direction, which is a predetermined reference axis direction, and a second direction, which is orthogonal to the first direction, and
   a bending resistance in the first direction of the adhesive patch measured by a 45° cantilever method defined in JIS L 1085:1998 is 18 to 30 mm.

2. The adhesive patch according to claim 1, wherein a basis weight of the nonwoven fabric is 90 to 110 g/m$^2$.

3. The adhesive patch according to claim 1, wherein a 20% modulus in a width direction of the nonwoven fabric is 3 to 5 N/50 mm.

4. The adhesive patch according to claim 1, wherein a 50% modulus in a width direction of the nonwoven fabric is 8 to 15 N/50 mm.

5. The adhesive patch according to claim 1, wherein the nonwoven fabric comprises a polyester.

6. The adhesive patch according to claim 1, wherein the bending resistance in the first direction of the adhesive patch measured by a 45° cantilever method defined in JIS L 1085:1998 is 18 to 27 mm.

\* \* \* \* \*